United States Patent
Siejko et al.

(10) Patent No.: US 7,963,926 B2
(45) Date of Patent: Jun. 21, 2011

(54) TRENDING OF SYSTOLIC MURMUR INTENSITY FOR MONITORING CARDIAC DISEASE WITH IMPLANTABLE DEVICE

(75) Inventors: Krzysztof Z. Siejko, Maple Grove, MN (US); Richard Fogoros, Pittsburg, PA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 481 days.

(21) Appl. No.: 12/220,710

(22) Filed: Jul. 28, 2008

(65) Prior Publication Data

US 2008/0294212 A1 Nov. 27, 2008

Related U.S. Application Data

(63) Continuation of application No. 11/122,749, filed on May 5, 2005, now Pat. No. 7,404,802.

(51) Int. Cl.
*A61B 5/02* (2006.01)
(52) U.S. Cl. .......................................... 600/528; 607/17
(58) Field of Classification Search .............. 607/6, 17; 600/513, 514, 521, 528
See application file for complete search history.

(56) References Cited

U.S. PATENT DOCUMENTS

| 4,094,308 A | 6/1978 | Cormier |
| 4,289,141 A | 9/1981 | Cormier |
| 4,446,872 A | 5/1984 | Marsoner et al. |
| 4,548,204 A | 10/1985 | Groch et al. |
| 4,649,930 A | 3/1987 | Groch et al. |
| 4,763,646 A | 8/1988 | Lekholm |
| 4,905,706 A | 3/1990 | Duff et al. |
| 4,915,113 A | 4/1990 | Holman |
| 4,989,611 A | 2/1991 | Zanetti et al. |
| 5,159,932 A | 11/1992 | Zanetti et al. |
| 5,365,932 A | 11/1994 | Greenhut |
| 5,496,361 A | 3/1996 | Moberg et al. |
| 5,554,177 A | 9/1996 | Kieval et al. |
| 5,674,256 A | 10/1997 | Carlson |
| 5,685,317 A | 11/1997 | Sjostrom |
| 5,687,738 A | 11/1997 | Shapiro et al. |
| 5,697,375 A | 12/1997 | Hickey |
| 5,700,283 A | 12/1997 | Salo |
| 5,836,987 A | 11/1998 | Baumann et al. |
| 5,991,661 A | 11/1999 | Park et al. |
| 6,044,298 A | 3/2000 | Salo et al. |

(Continued)

FOREIGN PATENT DOCUMENTS

WO WO-2004032741 A1 4/2004

(Continued)

OTHER PUBLICATIONS

"U.S. Appl. No. 11/122,749, Response filed Nov. 26, 2007 to Non-Final Office Action mailed Sep. 25, 2007", 9 pgs.

(Continued)

*Primary Examiner* — Carl H Layno
*Assistant Examiner* — Brian T Gedeon
(74) *Attorney, Agent, or Firm* — Schwegman, Lundberg & Woessner, P.A.

(57) ABSTRACT

Described is an implantable device configured to monitor for changes in the intensity and/or duration of a systolic murmur such as mitral regurgitation by means of an acoustic sensor. Such changes may be taken to indicate a change in a patient's heart failure status. Upon detection of a worsening in the patient's heart failure statue, the device may be programmed to alert clinical personnel over a patient management network and/or make appropriate adjustments to pacing therapy.

20 Claims, 4 Drawing Sheets

U.S. PATENT DOCUMENTS

| | | | |
|---|---|---|---|
| 6,044,299 | A | 3/2000 | Nilsson |
| 6,045,513 | A | 4/2000 | Stone et al. |
| 6,053,872 | A | 4/2000 | Mohler |
| 6,058,329 | A | 5/2000 | Salo et al. |
| 6,064,910 | A | 5/2000 | Andersson et al. |
| 6,077,227 | A | 6/2000 | Miesel |
| 6,152,884 | A | 11/2000 | Bjorgaas |
| 6,264,611 | B1 | 7/2001 | Ishikawa et al. |
| 6,298,269 | B1 | 10/2001 | Sweeney |
| 6,312,378 | B1 | 11/2001 | Bardy |
| 6,366,811 | B1 | 4/2002 | Carlson |
| 6,368,283 | B1 | 4/2002 | Xu et al. |
| 6,409,675 | B1 | 6/2002 | Turcott |
| 6,415,033 | B1 | 7/2002 | Halleck et al. |
| 6,440,082 | B1 | 8/2002 | Joo et al. |
| 6,477,406 | B1 | 11/2002 | Turcott |
| 6,527,729 | B1 | 3/2003 | Turcott |
| 6,572,560 | B1 | 6/2003 | Watrous et al. |
| 6,575,916 | B2 | 6/2003 | Halleck et al. |
| 6,643,548 | B1 | 11/2003 | Mai et al. |
| 6,650,940 | B1 | 11/2003 | Zhu et al. |
| 6,665,564 | B2 | 12/2003 | Lincoln et al. |
| 6,795,732 | B2 | 9/2004 | Stadler et al. |
| 6,810,287 | B2 | 10/2004 | Zhu et al. |
| 6,824,519 | B2 | 11/2004 | Narimatsu et al. |
| 6,830,548 | B2 | 12/2004 | Bonnet et al. |
| 6,845,263 | B2 | 1/2005 | Kawaguchi |
| 7,115,096 | B2 | 10/2006 | Siejko et al. |
| 7,123,962 | B2 | 10/2006 | Siejko et al. |
| 7,139,609 | B1 | 11/2006 | Min et al. |
| 7,142,920 | B2 | 11/2006 | Scheiner et al. |
| 7,404,802 | B2 | 7/2008 | Siejko et al. |
| 2002/0001390 | A1 | 1/2002 | Kawaguchi |
| 2002/0035337 | A1 | 3/2002 | Oka |
| 2002/0082645 | A1 | 6/2002 | Sweeney |
| 2002/0107450 | A1 | 8/2002 | Ogura |
| 2002/0147401 | A1 | 10/2002 | Oka |
| 2002/0151812 | A1 | 10/2002 | Scheiner et al. |
| 2002/0151938 | A1 | 10/2002 | Corbucci |
| 2003/0055352 | A1 | 3/2003 | Hayek et al. |
| 2003/0069608 | A1 | 4/2003 | Sweeney |
| 2003/0072458 | A1 | 4/2003 | Halleck et al. |
| 2003/0093002 | A1 | 5/2003 | Kuo |
| 2003/0093003 | A1 | 5/2003 | Watrous et al. |
| 2003/0120159 | A1 | 6/2003 | Mohler |
| 2003/0176896 | A1 | 9/2003 | Lincoln et al. |
| 2003/0208240 | A1 | 11/2003 | Pastore et al. |
| 2003/0216620 | A1 | 11/2003 | Jain et al. |
| 2003/0229289 | A1 | 12/2003 | Mohler |
| 2004/0024423 | A1 | 2/2004 | Lincoln et al. |
| 2004/0039419 | A1 | 2/2004 | Stickney et al. |
| 2004/0039420 | A1 | 2/2004 | Jayne et al. |
| 2004/0064056 | A1 | 4/2004 | Ogura |
| 2004/0078059 | A1 | 4/2004 | Ding et al. |
| 2004/0078060 | A1 | 4/2004 | Ding et al. |
| 2004/0106960 | A1 | 6/2004 | Siejko et al. |
| 2004/0106961 | A1 | 6/2004 | Siejko et al. |
| 2004/0127792 | A1 | 7/2004 | Siejko et al. |
| 2004/0138572 | A1 | 7/2004 | Thiagarajan |
| 2004/0167417 | A1 | 8/2004 | Schulhauser et al. |
| 2004/0215264 | A1 | 10/2004 | Van Bentem |
| 2004/0225332 | A1 | 11/2004 | Gebhardt et al. |
| 2004/0236239 | A1 | 11/2004 | Murray et al. |
| 2004/0254481 | A1 | 12/2004 | Brodnick |
| 2004/0260188 | A1 | 12/2004 | Syed et al. |
| 2004/0267147 | A1 | 12/2004 | Sullivan |
| 2004/0267148 | A1 | 12/2004 | Arand et al. |
| 2005/0027323 | A1 | 2/2005 | Mulligan et al. |
| 2005/0033190 | A1 | 2/2005 | Bauer |
| 2006/0253159 | A1 | 11/2006 | Siejko et al. |
| 2006/0282000 | A1 | 12/2006 | Zhang et al. |

FOREIGN PATENT DOCUMENTS

| | | | |
|---|---|---|---|
| WO | WO-2006121844 A2 | 11/2006 | |
| WO | WO-2006121844 A3 | 11/2006 | |

OTHER PUBLICATIONS

"U.S. Appl. No. 11/122,749, Response filed Sep. 18, 2007 to Final Office Action mailed Jul. 18, 2007", 14 pgs.

"U.S. Appl. No. 11/122,749, Supplemental Notice of Allowability mailed Apr. 17, 2008", 4 pgs.

"U.S. Appl. No. 11/122,749, Notice of Allowance mailed Mar. 25, 2008", 5 pgs.

"Final Office Action mailed Jul. 18, 2007 in U.S. Appl. No. 11/122,749", 11 pgs.

"Final-Office Action Mailed Sep. 25, 2007 in U.S. Appl. No. 11/122,749", 10 pgs.

"International Search Report and Written Opinion for Application No. PCT/US2006/017387, Date Mailed Oct. 20, 2006", 10 Pages.

TRENDING OF SYSTOLIC MURMUR INTENSITY FOR MONITORING CARDIAC DISEASE WITH IMPLANTABLE DEVICE

CROSS REFERENCE TO RELATED APPLICATION

This application is a continuation of U.S. application Ser. No. 11/122,749, now U.S. Pat. No. 7,404,802, filed May 5, 2005, the specification of which is herein incorporated by reference.

FIELD OF THE INVENTION

This invention pertains to cardiac devices such as pacemakers and other types of devices for monitoring and treating cardiac dysfunction.

BACKGROUND

Heart failure (HF) refers to a condition in which the heart fails to pump enough blood to satisfy the needs of the body. It is usually due to some damage to the heart itself, such as from a myocardial infarction or heart attack. When heart failure occurs acutely, autonomic circulatory reflexes are activated that both increase the contractility of the heart and constrict the vasculature as the body tries to defend against the drop in blood pressure. Venous constriction, along with the reduction in the heart's ability to pump blood out of the venous and pulmonary systems (so-called backward failure), causes an increase in the diastolic filling pressure of the ventricles. This increase in preload (i.e., the degree to which the ventricles are stretched by the volume of blood in the ventricles at the end of diastole) causes an increase in stroke volume during systole, a phenomena known as the Frank-Starling principle. If the heart failure is not too severe, this compensation is enough to sustain the patient at a reduced activity level. When moderate heart failure persists, other compensatory mechanisms come into play that characterize the chronic stage of heart failure. The most important of these is the depressing effect of a low cardiac output on renal function. The increased fluid retention by the kidneys then results in an increased blood volume and further increased venous return to the heart. A state of compensated heart failure results when the factors that cause increased diastolic filling pressure are able to maintain cardiac output at a normal level even while the pumping ability of the heart is compromised.

Compensated heart failure, however, is a precarious state. If cardiac function worsens or increased cardiac output is required due to increased activity or illness, the compensation may not be able to maintain cardiac output at a level sufficient to maintain normal renal function. Fluid then continues to be retained, causing the progressive peripheral and pulmonary edema that characterizes overt congestive heart failure. Diastolic filling pressure becomes further elevated which causes the heart to become so dilated and edematous that its pumping function deteriorates even more. This condition, in which the heart failure continues to worsen, is decompensated heart failure. It can be detected clinically, principally from the resulting pulmonary congestion and dyspnea, and all clinicians know that it can lead to rapid death unless appropriate therapy is instituted.

SUMMARY

Described herein is a method by which an implantable cardiac device may monitor a patient's heart failure status. The method involves measuring the intensity of a systolic murmur with an acoustic sensor incorporated into the device. Upon detecting an increase in the intensity of the murmur, the device may be configured to transmit an alarm message over a patient management network. In another embodiment, the device is configured to deliver pacing therapy which may be altered and/or initiated upon detection of an increase in murmur intensity.

DETAILED DESCRIPTION

The tricuspid and mitral valves, also referred to as the atrioventricular or AV valves, separate the atrium and ventricle on the right and left sides of heart, respectively. The function of the atrioventricular valves is to allow flow of blood between the atrium and ventricle during ventricular diastole and atrial systole but prevent the backflow of blood during ventricular systole. The mitral valve is composed of a fibrous ring called the mitral annulus located between the left atrium and the left ventricle, the anterior and posterior leaflets, the chordae tendineae, and the papillary muscles. The leaflets extend from the mitral annulus and are tethered by the chordae tendineae to the papillary muscles which are attached to the left ventricle. The function of the papillary muscles is to contract during ventricular systole and limit the travel of the valve leaflets back toward the left atrium. If the valve leaflets are allowed to bulge backward into the atrium during ventricular systole, called prolapse, leakage of blood through the valve can result. The structure and operation of the tricuspid valve is similar.

Mitral regurgitation (MR), also referred to as mitral insufficiency or mitral incompetence, is characterized by an abnormal reversal of blood flow from the left ventricle to the left atrium during ventricular systole. This occurs when the leaflets of the mitral valve fail to close properly as the left ventricle contracts, thus allowing retrograde flow of blood back into the left atrium. Tricuspid regurgitation (TR) occurs in a similar manner. MR and TR can be due to a variety of structural causes such as ruptured chordae tendineae, leaflet perforation, or papillary muscle dysfunction. Functional MR and TR may also occur in heart failure patients due to annular dilatation or myocardial dysfunction, both of which may prevent the valve leaflets from coapting properly.

In certain patients, the severity of MR is known to increase with worsening heart failure. In the events leading up to HF decompensation, the presence of volume and/or pressure overload and ventricular dilation result in advancement of valvular insufficiency due to, for example, extra tension on the papillary muscles and chordae tendineae as well as distortion of the mitral annulus. A worsening of left ventricular systolic function also implies an elevation of mean left atrial pressure which increases the severity of MR.

Described herein is system which may be incorporated into an implantable cardiac device with a capability of sensing murmurs is used to monitor changes in the intensity and duration of murmurs in a chronic ambulatory manner. In conjunction with an in-home or portable patient monitoring system by which the implantable device may transmit messages over a network, changes in the severity of systolic murmurs (such as MR) may be used to alert physicians and caregivers of worsening cardiac disease and, in particular, decompensated heart failure. Monitoring for changes in the severity of MR is a viable means for monitoring the severity of heart failure that is independent of other measures such as right-sided pressures, pulmonary fluid status, and respiration rate.

The system for sensing murmurs includes an acoustic sensor (e.g., a microphone or other type of pressure sensor) with sufficient bandwidth (e.g., 1 Khz) to detect at least moderate levels of systolic mitral valve insufficiency. In different embodiments, the acoustic sensor is a pressure sensor integrated with a pacing lead, a dedicated pressure sensor either leadless or with a lead, or a microphone mounted on the surface of the implantable device housing. Electrograms provided by the sensing channels of the implantable device may be used to identify the systolic phase of the cardiac cycle, and signal processing techniques may be used to detect and measure attributes of the murmur. These attributes can be measured repeatedly throughout the day and used to form a trend. The murmur baseline may be established during a period where the disease status of the patient is known to be stable. Significant changes from the baseline can be used to generate an alarm message, or can be combined with information from other sensors to make a blended sensor decision.

In an exemplary embodiment, envelope detection of broadband acoustic energy in a band between 200 Hz and up to 1 Khz is used to measure murmur intensity. Harmonic heart sound components (e.g., S1 and S2) may be filtered out or ignored. Measurement of the intensity, duration and timing of the murmur relative to the systolic phase of the cardiac cycle are made and may be repeated multiple times. The multiple measurements can be statistically combined to generate a composite daily measurement. The algorithm for detection of a significant change in the murmur may also take into account the variability of the daily measurements by using tests of statistical significance to declare those measurements that are different from an established baseline, thus offering a means of adjustment of sensitivity and specificity.

Described below is an exemplary implantable device into which may be incorporated a system for monitoring systolic murmur intensity. The device may or may not include other functionality such as cardiac pacing. As is explained, however, in a device with pacing functionality, changes in systolic murmur intensity may also be used to trigger compensatory alterations in pacing therapy.

1. Exemplary Device Description

Figure 1:
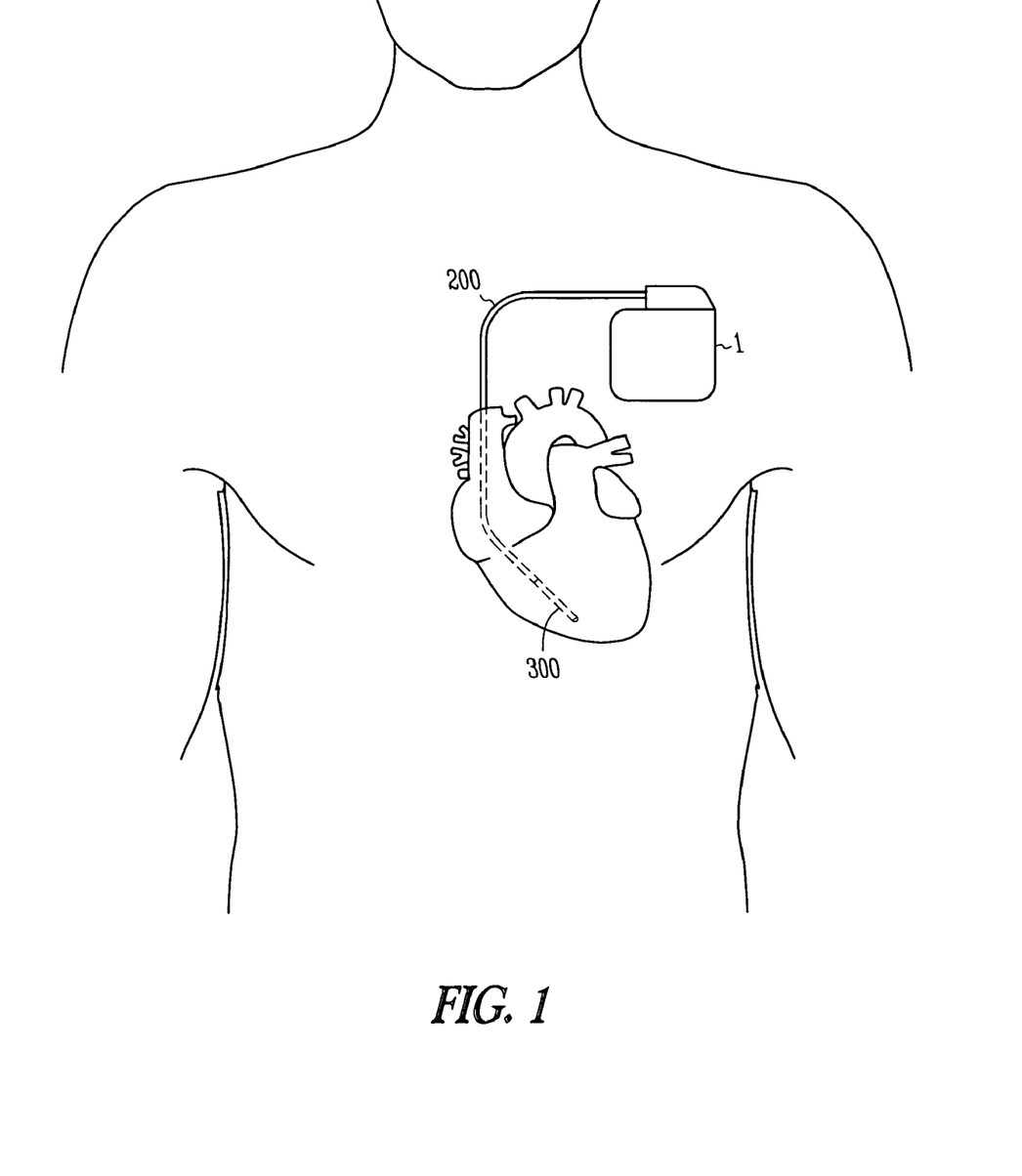
FIG. 1 illustrates the physical placement of an implantable cardiac device.

As shown in FIG. 1, an implantable cardiac device 1 for delivering pacing therapy (a.k.a., a pacemaker) is typically placed subcutaneously or submuscularly in a patient's chest with leads 200 threaded intravenously into the heart to connect the device to electrodes 300 used for sensing and pacing of the atria and/or ventricles. Electrodes may also be positioned on the epicardium by various means. A programmable electronic controller causes the pacing pulses to be output in response to lapsed time intervals and sensed electrical activity (i.e., intrinsic heart beats not as a result of a pacing pulse). The device senses intrinsic cardiac electrical activity through a sensing channel which incorporates internal electrodes disposed near the chamber to be sensed. A depolarization wave associated with an intrinsic contraction of the atria or ventricles that is detected by the device is referred to as an atrial sense or ventricular sense, respectively. In order to cause such a contraction in the absence of an intrinsic beat, a pacing pulse with energy above a certain threshold is delivered to the chamber through a pacing channel which incorporates internal electrodes disposed near the chamber to be paced.

Figure 2:
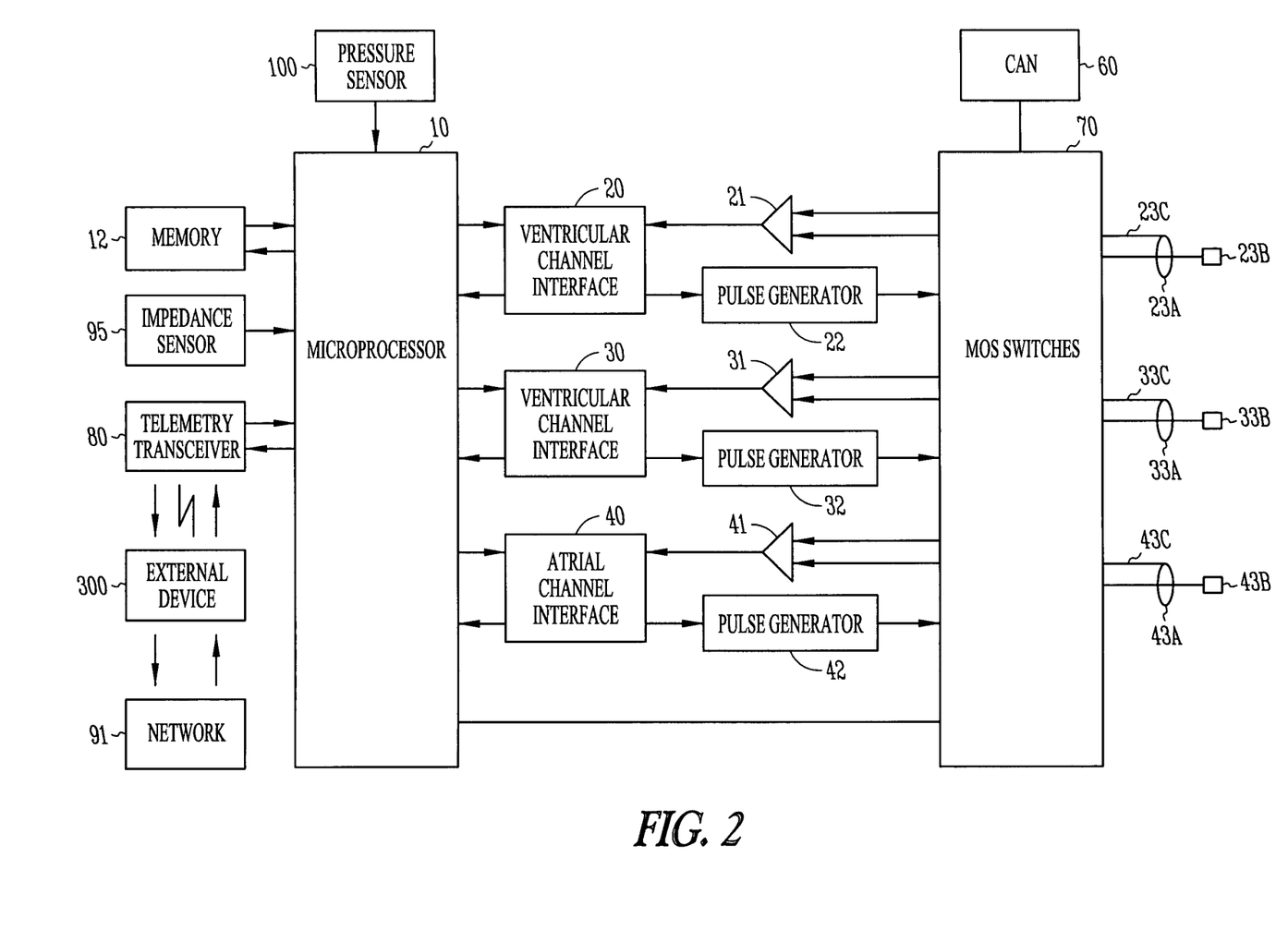
FIG. 2 illustrates an exemplary implantable device for monitoring systolic murmurs as well as delivering pacing therapy.

A block diagram of an implantable multi-site pacemaker having multiple sensing and pacing channels is shown in FIG. 2. The controller of the pacemaker is made up of a microprocessor 10 communicating with a memory 12 via a bidirectional data bus, where the memory 12 typically comprises a ROM (read-only memory) for program storage and a RAM (random-access memory) for data storage. The controller is capable of operating the pacemaker in a number of programmed modes where a programmed mode defines how pacing pulses are output in response to sensed events and expiration of time intervals. A telemetry transceiver 80 is provided for communicating with an external device 300 such as an external programmer. An external programmer is a computerized device with an associated display and input means that can interrogate the pacemaker and receive stored data as well as directly adjust the operating parameters of the pacemaker. The telemetry transceiver 80 enables the controller to communicate with an external device 300 via a wireless telemetry link. The external device 300 may be an external programmer which can be used to program the implantable device as well as receive data from it or may be a remote monitoring unit. The external device 300 may also be interfaced to a patient management network 91 enabling the implantable device to transmit data and alarm messages to clinical personnel over the network as well as be programmed remotely. The network connection between the external device 300 and the patient management network 91 may be implemented by, for example, an internet connection, over a phone line, or via a cellular wireless link.

The embodiment shown in FIG. 2 has multiple sensing/pacing channels, where a pacing channel is made up of a pulse generator connected to an electrode while a sensing channel is made up of the sense amplifier connected to an electrode. A MOS switching network 70 controlled by the microprocessor is used to switch the electrodes from the input of a sense amplifier to the output of a pulse generator. The switching network 70 also allows the sensing and pacing channels to be configured by the controller with different combinations of the available electrodes. The channels may be configured as either atrial or ventricular channels allowing the device to deliver conventional ventricular single-site pacing, biventricular pacing, or multi-site pacing of a single chamber, where the ventricular pacing is delivered with or without atrial tracking. In an example configuration, three representative sensing/pacing channels are shown. A right atrial sensing/pacing channel includes ring electrode 43a and tip electrode 43b of bipolar lead 43c, sense amplifier 41, pulse generator 42, and a channel interface 40. A right ventricular sensing/pacing channel includes ring electrode 23a and tip electrode 23b of bipolar lead 23c, sense amplifier 21, pulse generator 22, and a channel interface 20, and a left ventricular sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In this embodiment, the device is equipped with bipolar leads that include two electrodes which are used for outputting a pacing pulse and/or sensing intrinsic activity. Other embodiments may employ unipolar leads with single electrodes for sensing and pacing. The switching network 70 may configure a channel for unipolar sensing or pacing by referencing an electrode of a unipolar or bipolar lead with the device housing or can 60.

The controller controls the overall operation of the device in accordance with programmed instructions stored in memory and implements the systolic murmur monitoring function as described herein. The controller interprets electrogram signals from the sensing channels, implements timers for specified intervals, and controls the delivery of paces in accordance with a pacing mode. The sensing circuitry of the pacemaker generates atrial and ventricular electrogram signals from the voltages sensed by the electrodes of a particular channel. An electrogram indicates the time course and amplitude of cardiac depolarization and repolarization that occurs during either an intrinsic or paced beat. When an electrogram signal in an atrial or ventricular sensing channel exceeds a specified threshold, the controller detects an atrial or ventricular sense, respectively, which pacing algorithms may employ to trigger or inhibit pacing. An impedance sensor 95 is also interfaced to the controller for measuring transthoracic impedance. The transthoracic impedance measurement may be used to derive either respiratory minute ventilation for rate-adaptive pacing modes or, as described below, cardiac stroke volume for monitoring heart failure status.

2. Exemplary System for Monitoring Systolic Murmurs

Figure 3:
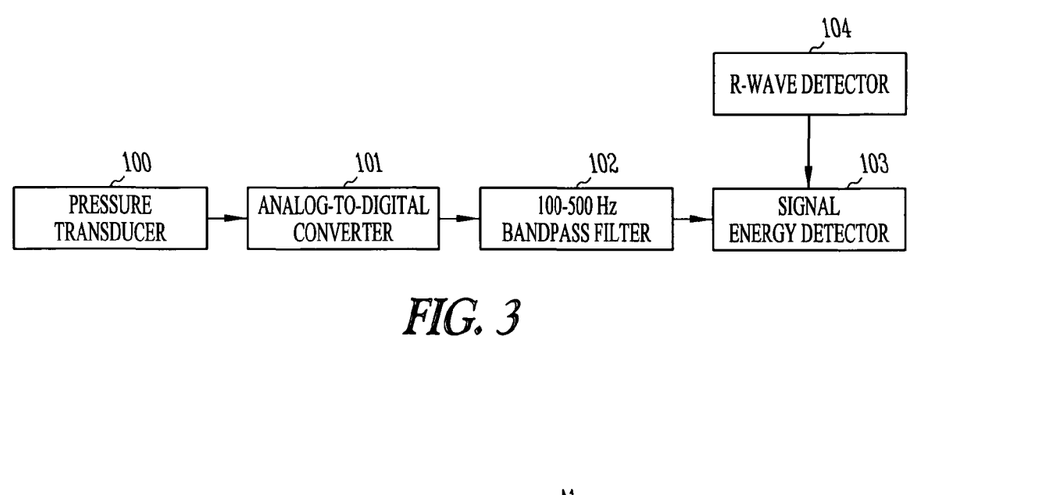
FIG. 3 is a block diagram of a system for measuring systolic murmur intensity.

Also shown in FIG. 2 is a pressure sensor 100 which is interfaced to the controller and allows the device to monitor for changes in the intensity or duration in a systolic murmur such as MR. FIG. 3 illustrates a particular embodiment of a system for sensing a systolic murmur which may be incorporated into the implantable device. The pressure sensor 100 is adapted for disposition so as to sense the acoustic vibrations produced by a systolic murmur (e.g., disposed in the pulmonary artery) and is connected to the implantable device by an intravascular lead or a lead-less type of link (e.g., an ultrasonic or RF link). After digitization by analog-to-digital converter 101, the signal from the pressure sensor 100 is filtered by a bandpass filter 102 which may be implemented in code executed by the device controller. In this example, the filter's passband is from 100 Hz to 500 Hz which represents a band which is fairly specific for the frequency components of a murmur due to MR. Other passbands could be used to tailor the filtering for a patient's specific murmur. The filtered pressure signal is next passed to a signal energy detector 103, also implemented as code executed by the controller, which measures the signal energy in the filtered pressure signal which may be taken to represent the intensity of the murmur. An R-wave detector (i.e., detection of a ventricular sense by the device) 104 enables the energy detector to measure the intensity of the murmur during the systolic phase of the cardiac cycle. The controller may also measure the duration of the murmur during the systolic phase. Changes in either the intensity or duration of the murmur from baseline values may be used as an indicator of a change in the patient's heart failure status.

Figure 4:
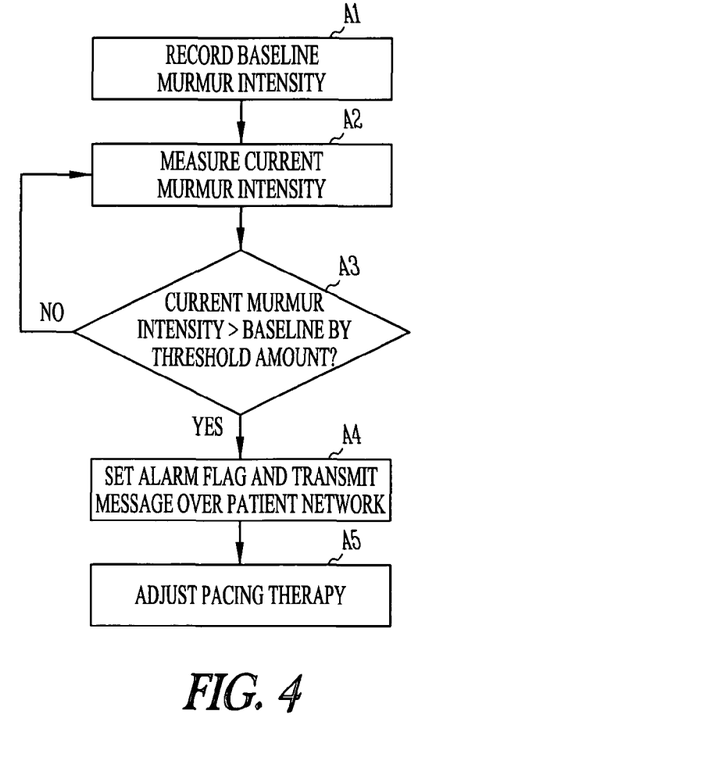
FIGS. 4 and 5 illustrate exemplary algorithms which may be implemented in an implantable device.

FIG. 4 illustrates an exemplary algorithm which may be executed by the controller to monitor for changes in a systolic murmur and report such changes to clinical personnel so that intervention may be initiated if appropriate. At step A1, the patient's baseline murmur intensity is recorded. At step A2, the patient's current murmur intensity is measured, where the current murmur intensity may be an average of intensity measurements taken over some period of time in order to average out insignificant variations. At step A3, the current murmur intensity is compared with the baseline value to determine if the intensity has increased by a specified threshold amount. If not, steps A2 and A3 are repeated on a continuous or periodic basis. If the murmur intensity has increased by the specified threshold amount, an alarm flag is set and an alarm message is transmitted to over the patient management network via telemetry at step A4. If the device is configured to deliver pacing therapy, such therapy may also be adjusted at step A5 in response to the change in murmur intensity. As explained below, such pacing therapy adjustments may involve cardiac resynchronization pacing.

Figure 5:
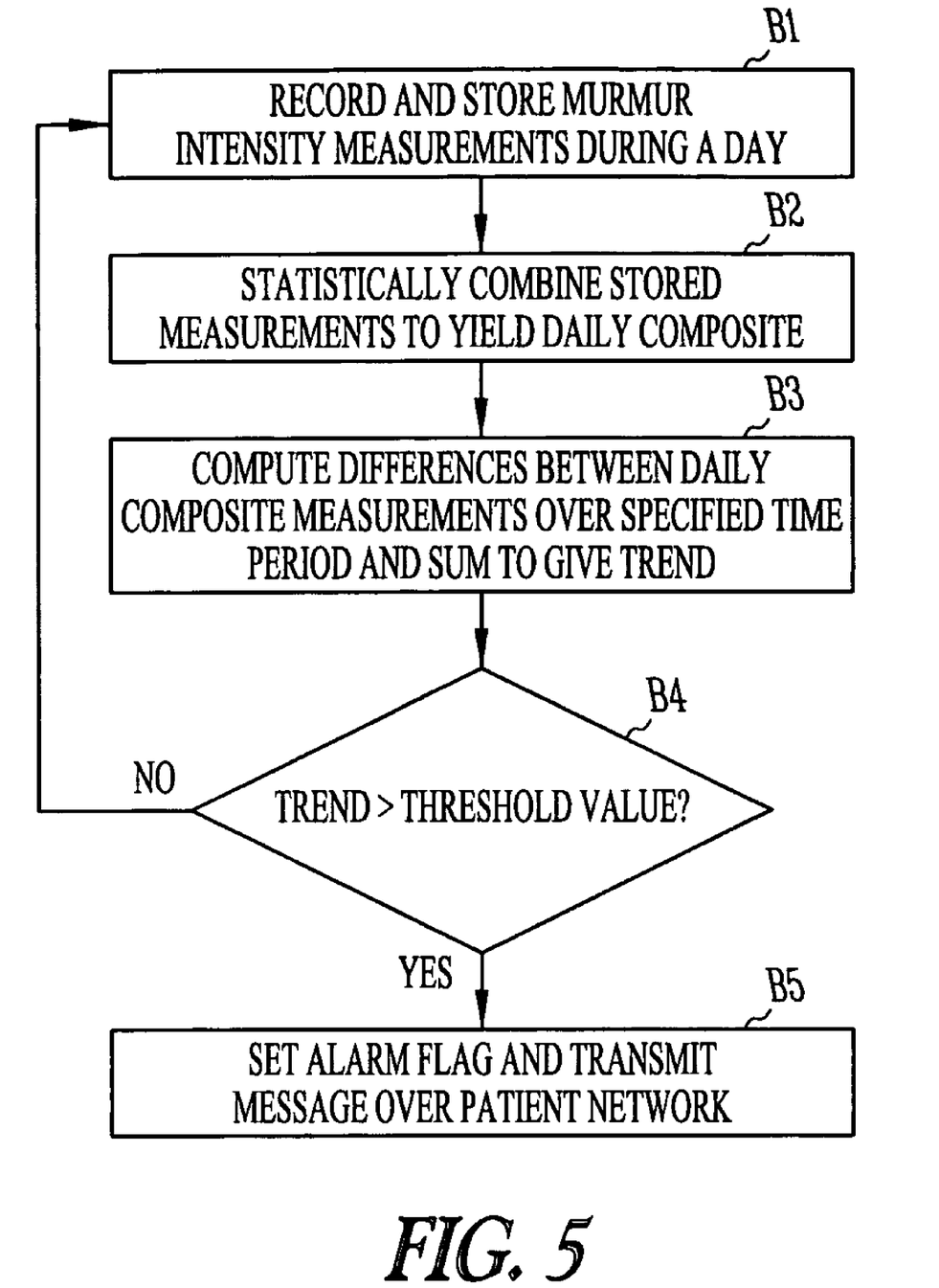

The device may also record the murmur intensity measurements in order to determine if a trend exists. For example, if the device determines that the patient's murmur intensity is increasing at a rate above a specified threshold value, an alarm flag could be set and an alarm message sent over the patient management network even if the murmur intensity is not above the baseline value by the specified threshold amount. Automatic adjustments to pacing therapy could also be made in response to a detected trend. FIG. 5 illustrates an exemplary algorithm. At step B1, multiple intensity measurements are taken during the day (or other defined time period) and stored. At step B2, the stored intensity measurements are statistically combined (e.g., averaged) to yield a composite intensity measurement for the day. At step B3, the positive or negative differences between consecutive daily composite intensity measurements over some period of time (e.g., a week or a month) are computed and summed to give the net increase or decrease in intensity over the period of time, thus representing the trend in the murmur's intensity. This trend is then compared with a specified threshold value at step B4. If the trend is positive and greater than the threshold, an alarm flag is set and an alarm message is transmitted to over the patient management network via telemetry at step B5.

The algorithms discussed above with reference to FIGS. 4 and 5 monitor for changes in murmur intensity as an indicator of heart failure status. The same steps could also be performed with respect to murmur duration as changes in the duration of a systolic murmur can also be due to changes in heart failure status. Also, the device may use other sensing modalities to monitor for changes in other parameters besides murmur intensity and duration which may be indicative of either worsening MR or heart failure. Changes in these additional parameters may then be used by the device to more specifically detect if a change in heart failure status has taken place. For example, if the pressure sensor is disposed in the pulmonary artery, the device may measure the pulmonary pressure as an estimate of mean left atrial pressure which increases as the severity of MR increases. The device could then be programmed to set an alarm flag if the current murmur intensity exceeds the baseline murmur intensity by a specified threshold amount only if the left atrial pressure during also exceeds another specified threshold amount. Another way in which the extent of mitral regurgitation and/or heart failure status may be monitored is via a transthoracic impedance measurement reflective of cardiac volume during the cardiac cycle. As mitral regurgitation produces volume overloading of both the left atrium and ventricle, an increase in, for example, end-diastolic left ventricular volume above a specified threshold may be used as an indication that the patient's MR or heart failure has worsened.

As noted above, changes in a patient's heart failure status as detected by systolic murmur monitoring may also be used to adjust pacing therapy delivered by the device. Ventricular resynchronization therapy is most commonly applied in the treatment of patients with heart failure due to left ventricular dysfunction which is either caused by or contributed to by left ventricular conduction abnormalities. In such patients, the left ventricle or parts of the left ventricle contract later than normal during systole which thereby impairs pumping efficiency. In order to resynchronize ventricular contractions in such patients, pacing therapy is applied such that the left ventricle or a portion of the left ventricle is pre-excited relative to when it would become depolarized in an intrinsic contraction. Optimal pre-excitation for treating a conduction deficit in a given patient may be obtained with biventricular pacing or with left ventricular-only pacing. If the device is configured to deliver resynchronization therapy, such therapy could be initiated upon detection of a worsening in the patient's heart failure status. Alternatively, pacing parameters could be adjusted in order to increase the amount of pre-excitation delivered by the therapy. For example, the AV delay used in atrial tracking pacing modes could be decreased, or the biventricular offset used to pre-excite one ventricle (usually the left ventricle) could be increased.

In an exemplary embodiment, an implantable cardiac device comprises a pressure sensor adapted for disposition so as to sense the acoustic vibrations produced by a systolic murmur; a bandpass filter for filtering the pressure signal; a signal energy detector for measuring a parameter related to the signal energy of the filtered pressure signal to represent the murmur intensity; a controller programmed to record a baseline murmur intensity; and, wherein the controller is further programmed to measure a current murmur intensity as an average of intensity measurements taken over some period of time, compare the current murmur intensity to the baseline murmur intensity, and set an alarm flag if the current murmur intensity exceeds the baseline murmur intensity by a specified threshold amount. The device may further comprise a pressure sensor adapted for disposition in the pulmonary artery which is configured to measure the pulmonary pressure and wherein the controller is programmed to set an alarm flag if the current murmur intensity exceeds the baseline murmur intensity by a specified threshold amount only if the pulmonary pressure also exceeds another specified threshold amount.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. An implantable cardiac device, comprising:
   a pressure sensor adapted for disposition so as to sense the acoustic vibrations produced by a systolic murmur and produce a pressure signal reflective thereof;
   circuitry for measuring the intensity of the systolic murmur from the pressure signal produced by the pressure sensor;
   an impedance sensor configured to measure transthoracic impedance reflective of cardiac volume;
   a controller programmed to record a baseline murmur intensity; and,
   wherein the controller is further programmed to measure a current murmur intensity as an average of intensity measurements taken over some period of time, compare the current murmur intensity to the baseline murmur intensity, and detect a change indicative of worsening cardiac status if the current murmur intensity exceeds the baseline murmur intensity by a first specified threshold amount and if the transthoracic impedance measurement indicates an increase in cardiac volume above a second specified threshold amount.

2. The device of claim 1 wherein the controller is programmed to measure a current duration of the murmur during the systolic phase, compare the current murmur duration to a baseline murmur duration, and set an alarm flag if the current murmur duration exceeds the baseline murmur duration by the first specified threshold amount.

3. The device of claim 1 further comprising a signal energy detector and an R-wave detector for enabling the signal energy detector to measure the intensity of the murmur during the systolic phase of the cardiac cycle.

4. The device of claim 1 further comprising a telemetry transceiver and wherein the controller is programmed to transmit an alarm message over a patient management network via telemetry if the current murmur intensity exceeds the baseline murmur intensity by the first specified threshold amount.

5. The device of claim 1 wherein the controller is further programmed to store the current murmur intensity measurements take over a specified period time and compute a trend in the murmur's intensity.

6. The device of claim 5 wherein the trend is computed by computing differences between consecutive current murmur intensity measurements over the specified period of time and summing the differences.

7. The device of claim 1 further comprising:
   a bandpass filter for filtering the pressure signal; and,
   a signal energy detector for measuring a parameter related to the signal energy of the filtered pressure signal to represent the murmur intensity.

8. The device of claim 1 further comprising circuitry for pacing the heart in a programmed mode and wherein the controller is programmed to adjust the programmed mode if the current murmur intensity exceeds the baseline murmur intensity by a specified threshold amount.

9. The device of claim 8 wherein the device is configured to pace the heart in an atrial triggered mode and wherein the controller is programmed to adjust a programmed AV delay if the current murmur intensity exceeds the baseline murmur intensity by a specified threshold amount.

10. The device of claim 8 wherein the device is configured to pace the heart in a biventricular pacing mode and wherein the controller is programmed to adjust a biventricular offset if the current murmur intensity exceeds the baseline murmur intensity by the first specified threshold amount.

11. A method, comprising:
    producing a pressure signal reflective of the acoustic vibrations produced by a systolic murmur;
    filtering the pressure signal;
    measuring a parameter related to the signal energy of the filtered pressure signal to represent the murmur intensity;
    recording a baseline murmur intensity;
    measuring transthoracic impedance reflective of cardiac volume; and,
    measuring a current murmur intensity as an average of intensity measurements taken over some period of time, comparing the current murmur intensity to the baseline murmur intensity, and detecting a change indicative of worsening cardiac status if the current murmur intensity exceeds the baseline murmur intensity by a first specified threshold amount and if the transthoracic impedance measurement indicates an increase in cardiac volume above a second specified threshold amount.

12. The method of claim 11 further comprising measuring a current duration of the murmur during the systolic phase, comparing the current murmur duration to a baseline murmur duration, and setting an alarm flag if the current murmur duration exceeds the baseline murmur duration by the first specified threshold amount.

13. The method of claim 11 further comprising detecting R-waves in order to measure the intensity of the murmur during the systolic phase of the cardiac cycle.

14. The method of claim 11 further comprising transmitting an alarm message over a patient management network via telemetry if the current murmur intensity exceeds the baseline murmur intensity by the first specified threshold amount.

15. The method of claim 11 further comprising storing the current murmur intensity measurements take over a specified period time and computing a trend in the murmur's intensity.

16. The method of claim 15 wherein the trend is computed by computing differences between consecutive current murmur intensity measurements over the specified period of time and summing the differences.

17. The method of claim 11 further comprising measuring the pulmonary pressure and setting an alarm flag if the current murmur intensity exceeds the baseline murmur intensity by the first specified threshold amount and if the pulmonary pressure also exceeds another specified threshold amount.

18. The method of claim 11 further comprising pacing the heart in a programmed mode and adjusting the programmed mode if the current murmur intensity exceeds the baseline murmur intensity by a specified threshold amount.

19. The method of claim 18 further comprising pacing the heart in an atrial triggered mode and adjusting a programmed AV delay if the current murmur intensity exceeds the baseline murmur intensity by a specified threshold amount.

20. The method of claim 18 further comprising pacing the heart in a biventricular pacing mode and adjusting a biventricular offset if the current murmur intensity exceeds the baseline murmur intensity by a specified threshold amount.

* * * * *